United States Patent [19]

Fraiser et al.

[11] Patent Number: 5,536,649
[45] Date of Patent: Jul. 16, 1996

[54] DECONTAMINATION OF NUCLEIC ACID AMPLIFICATION REACTIONS USING URACIL-N-GLYCOSYLASE (UDG)

[75] Inventors: Melinda S. Fraiser, Durham; George T. Walker, Chapel Hill; James L. Schram, Knightdale, all of N.C.

[73] Assignee: Becton, Dickinson and Company, Franklin Lakes, N.J.

[21] Appl. No.: 283,117

[22] Filed: Jul. 29, 1994

Related U.S. Application Data

[63] Continuation-in-part of Ser. No. 60,842, May 11, 1993, abandoned.

[51] Int. Cl.$^6$ .............................. C12P 19/34; C12Q 1/68
[52] U.S. Cl. ................................................ 435/91.2; 435/6
[58] Field of Search ......................................... 435/6, 91.2

[56] References Cited

U.S. PATENT DOCUMENTS 5,035,996  7/1991  Hartley .
5,418,149  5/1985  Gelfand et al. ....................... 435/91.2

FOREIGN PATENT DOCUMENTS 0401037  12/1990  European Pat. Off. .
0415755  3/1991  European Pat. Off. .
WO92/01814  2/1992  WIPO .

OTHER PUBLICATIONS

Lu et al., (Sep. 1993), "Use of glycerol for enhanced efficiency and specificity of PCR amplification", Trends Genet. 9(9):297.

Shen et al., (1992), "DMSO improves PCR amplification of DNA with complex secondary structure", Trends Genet. 8(7):227.

Weiss et al., (1992), "Classification of subgroups of *Giardia lamblia* based upon ribosomal RNA gene sequence using the polymerase chain reaction", Mol. Biochem. Parasitol. 54:73–86.

C. G. Thornton, et al., "Utilizing Uracil DNA Glycosylaase to Control Carryover Contamination in PCR: Characterization of Residual UDG Activity Following Thermal Cycling" BioTechniques 13:180–184 (1992).

Z. Wang, et al., "Uracil–DNA Glycosylase Inhibitor of Bacteriophage PBS2: Cloning and Effects of Expression of the Inhibitor Gene in *Escherichia coli*" J. Bacteriol. 170:1082–1091 (1988).

B. K. Duncan, et al. "The cloning and overproduction of *Escherichia coli* uracil–DNA glycosylase" Gene 28:211–219 (1984).

T. Lindahl, et al. "DNA N–Glycosidases" J. Biol. Chem. 252:3286–3294 (1977).

X. Wang, et al. "Prevention of Carryover Contamination in the Detection of $\beta^s$ and $\beta^c$ Genes by Polymerase Chain Reaction" Am. J. Hemat. 40:146–148 (1992).

J. K. Ball, et al. "The use of uracil–N–glycosylase in the preparation of PCR products for direct sequencing" Nuc. Acids Res. 20:3255–3256 (1992).

J. Pang, et al. "Use of modified nucleotides and uracil–DNA glycosylase (UNG) for the control of contamination in the PCR–based amplification of RNA" Molec. Cell. Probes 6:251–256 (1992).

U. Varshney, et al. "Sequence Analysis, Expression, and Conservation of Escherichia coli Uracil DNA Glycosylase and Its Gene (ung)", J. Biol. Chem. 263:7776–7784 (1988).

U. Varshney, et al. "Specificities and Kinetics of Uracil Excision from Uracil–Containing DNA Oligomers by Escherichia coli Uracil DNA Glycosylase" Biochem. 30:4055–4061 (1991).

M. C. Longo, et al. "Use of uracil DNA glycosylase to control carry–over contamination in polymerase chain reactions" Gene 93:125–128 (1990).

R. Cone, et al. "Inhibitor of Uracil–DNA Glycosylase Induced by Bacteriophage PBS2" J. Biol. Chem. 255:10354–10358 (1980).

Z. Wang, et al., "Uracil–DNA Glycosylase Inhibitor Gene of Bacteriophage PBS2 Encodes a Binding Protein Specific for Uracil–DNA Glycosylase"J. Biol. Chem. 264:1163–1171 (1989).

P. Karran, et al. "Specificity of the Bacteriophage PBS2 Induced Inhibitor of Uracil–DNA Glycosylase" Biochem. 20:6092–6096 (1981).

Z. Wang et al. "Overproduction and characterization of the uracil–DNA glycosylase inhibitor of bacteriophage PBS2" Gene 99:31–37 (1991).

G. T. Walker, et al. "Isothermal in vitro amplification of DNA by a restriction enzyme/DNA polymerase system" Proc. Natl. Acad. Sci. USA 89:392–396 (1992).

Primary Examiner—W. Gary Jones
Assistant Examiner—Jeffrey Fredman
Attorney, Agent, or Firm—Donna R. Fugit

[57] ABSTRACT

Methods for inactivating contaminating amplicons in isothermal nucleic acid amplification reactions such as SDA. Uracil is incorporated into the amplicons produced by amplification in the place of thymine (T) using novel SDA reaction conditions. If these amplicons contaminate a subsequent amplification reaction, they may be inactivated as templates (i.e., rendered unamplifiable) by treatment with UDG. As isothermal amplification does not involve elevated temperatures, the UDG may be inactivated during the subsequent amplification of specific target sequences by inclusion of the UDG inhibitor protein Ugi. Incorporation of dU has unexpectedly been found to enhance the amplification power of SDA as compared to conventional SDA reactions. The methods may also be used to detect UDG activity in reagents or samples.

13 Claims, 2 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( x i ) SEQUENCE DESCRIPTION: SEQ ID NO:1:

TTGAATAGTC GGTTACTTGT TGACGGCGTA CTCGACC    37

( 2 ) INFORMATION FOR SEQ ID NO:2:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( x i ) SEQUENCE DESCRIPTION: SEQ ID NO:2:

TTGAAGTAAC CGACTATTGT TGACACTGAG ATCCCCT    37

( 2 ) INFORMATION FOR SEQ ID NO:3:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( x i ) SEQUENCE DESCRIPTION: SEQ ID NO:3:

TGGACCCGCC AAC    13

( 2 ) INFORMATION FOR SEQ ID NO:4:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( x i ) SEQUENCE DESCRIPTION: SEQ ID NO:4:

CGCTGAACCG GAT    13

( 2 ) INFORMATION FOR SEQ ID NO:5:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:5:

CGTTATCCAC CATAC    15

DECONTAMINATION OF NUCLEIC ACID AMPLIFICATION REACTIONS USING URACIL-N-GLYCOSYLASE (UDG)

This patent application is a continuation-in-part of U.S. patent application Ser. No. 08/060,842, filed May 11, 1993, abandoned.

FIELD OF THE INVENTION

The present invention relates to nucleic acid amplification and in particular to inactivation of amplicons from a previous amplification reaction which may contaminate a subsequent amplification reaction.

BACKGROUND OF THE INVENTION

Nucleic acid amplification reactions are processes by which specific nucleic acid sequences are amplified. The specific nucleic acid sequences to be amplified are referred to as target sequences. Amplification methods have become powerful tools in nucleic acid analysis and preparation. Several nucleic acid amplification methods are known. These include the polymerase chain reaction (PCR), self-sustained sequence replication (3SR), the ligase chain reaction (LCR), Qβ replicase amplification and strand displacement amplification (SDA). Unfortunately, the powerful ability of these nucleic acid amplification methods to amplify minute quantities of a target sequence also make them susceptible to contamination by copies of target sequences (amplicons) which may be carried over from previous amplification reactions in reagents, pipetting devices and laboratory surfaces. These contaminating products of previous amplifications may themselves be amplified in a subsequent amplification reaction. Even a few molecules of a contaminating target sequence may be readily amplified and detected, resulting in falsely positive results.

A recently developed method for inactivating contaminating amplicons in PCR involves incorporation of the nucleotide deoxyuridine triphosphate (dUTP) into amplified nucleic acid sequences in place of thymidine triphosphate (TTP). As deoxyuridine (dU) is not normally found in naturally-occurring DNA, this nucleotide serves to distinguish previously produced amplicons from new target sequences which have not yet been amplified. The uracil-containing DNAs, representing previously amplified contaminating sequences, are then treated with the enzyme uracil DNA glycosylase (UDG; also known as uracil N-glycosylase or UNG). In nature, uracil DNA glycosylase excises uracil bases from DNA which can arise as a result of either misincorporation by DNA polymerase or deamination of cytosine. For decontamination of PCR amplifications, UDG removes the intentionally incorporated uracil in amplified nucleic acid. Uracil is removed without destruction of the sugar-phosphodiester backbone, thereby producing an abasic site in the DNA. These abasic sites are susceptible to hydrolysis by heat or alkali, a process which fragments the uracil-containing DNA and renders it unamplifiable in subsequent PCR.

As employed to decontaminate PCR, a sample is treated with UDG prior to PCR amplification and the enzyme is inactivated prior to beginning the amplification reaction. This prevents removal of uracil residues from newly generated amplicons. PCR involves cycling between elevated and reduced temperatures. UDG is therefore inactivated after the decontamination treatment by incubation at high temperatures (70°–80° C.), a process which is compatible with the PCR. UDG is substantially inactive at the elevated temperatures used for the PCR amplification reactions themselves. However, it has been shown that upon return of the PCR sample to 4°–25° C. after amplification, sufficient UDG activity is still present to degrade dU-PCR amplification products. It has therefore been recommended that PCR reactions be maintained at elevated temperatures after UDG treatment (Rashtchian, A., Hartley, J. L. and Thornton, C. G., *Biotechniques*, volume 13, No. 2, page 180). To address the problem of residual UDG activity after heat inactivation, WO 92/01814 describes a thermolabile UDG enzyme. In a further attempt to control residual UDG activity still present after heat inactivation, Rashtchian, et al. have added a protein inhibitor of UDG (Ugi - uracil DNA glycosylase inhibitor) to PCR after heat inactivation of UDG. Ugi is a product of the bacteriophage PBS2 and inhibits host UDG to protect the phage genome during infection, as the phage substitutes dU for T during replication of its genome (Mosbaugh, D. W. and Wang, Z., *Journal of Bacteriology*, volume 170, No. 3 p.1082). Prior to the present invention, however, there has been no report suggesting the use of Ugi alone to inactivate UDG in the context of decontamination of nucleic acid amplification reactions.

In contrast to the PCR, several nucleic acid amplification methods are isothermal. That is, they do not involve the high/low temperature cycling of the PCR. Examples of isothermal amplification protocols are self-sustained sequence replication (3SR; J. C. Guatelli, et al. *PNAS* 87:1874–1878 (1990), Qβ replicase (P. M. Lizardi, et al. *Bio/Technology* 6:1197–1202 (1988), and Strand Displacement Amplification (SDA; G. T. Walker, et al. *PNAS* 89:392–396 (1992); G. T. Walker, et al. *Nuc. Acids Res.* 20:1691–1696 (1992)). Such isothermal amplification protocols present a particular problem for decontamination, as high temperature steps for inactivation of UDG may not be compatible with the reduced temperature and isothermal nature of the reaction. The SDA amplification protocol is particularly unusual in that it uses both a restriction enzyme and a polymerase to amplify DNA. DNA may be amplified by a factor of $10^8$ using this method. The power of the SDA system necessitates the development of a technique to insure that previously amplified material (amplicons) do not inadvertently contaminate fresh reactions. Such contamination may create falsely positive samples. The restriction enzyme most commonly used in SDA, HincII, recognizes a specific six base pair recognition sequence. SDA requires the incorporation of an α-thio derivative of deoxyadenine ($dA_S$) into the recognition site of HincII by the polymerase in lieu of the naturally occurring dA. The mechanism of SDA is such that the SDA primers form one strand of the restriction site and the polymerase extends the primer to complete the other strand of the site using $dA_S$TP. The $dA_S$ moiety 3' to the cut site inhibits the restriction of the modified strand. However, it does not inhibit the restriction of the unmodified strand donated by the primer.

Isothermal amplification reactions do not involve elevated temperatures as the PCR does, and it was therefore unknown prior to the present invention whether inclusion of an inhibitor of UDG alone (rather than in conjunction with heat inactivation) would be sufficient to prevent removal of uracil from the desired amplification products. Also, as the literature relating to UDG in PCR emphasizes the role of fragmentation of the abasic nucleic acids in amplicon inactivation (usually by heat), it was not previously known if removal of uracil alone would be sufficient to inactivate contaminating amplicons as templates for further amplification.

In addition to its isothermal nature, SDA differs from the PCR in several other important respects, all of which could have significant effects on the use of UDG for inactivation of contaminating amplicons. First, SDA requires nicking of the DNA by a restriction enzyme, and it has been shown that incorporation of uracil into restriction enzyme recognition sites in some cases prevents restriction. SDA also requires enzymatic displacement of the extended amplification product from the template strand by the polymerase. It was not known prior to the present invention whether 1) inclusion of uracil in the HincII restriction site and in the amplification product would prevent nicking by HincII (especially as uracil would be base paired with $dA_S$), and/or 2) the presence of uracil or uracil base-paired with α-thio-A would prevent normal strand displacement. It was also not known whether the polymerase could successfully incorporate both unconventional nucleotides (i.e., dUTP and $dA_STP$) into amplification products simultaneously. In addition, the SDA $KPO_4$ buffer system is unique in amplification reactions (PCR uses a Tris buffer) and it was not known if UDG and Ugi would be active in a $KPO_4$ buffer system.

In order to apply UDG decontamination to amplicons generated by SDA, it was essential that dUTP first be incorporated into amplicons (copies of a target sequence generated during the amplification reaction) via SDA. However, simple substitution of dUTP for TTP in the conventional SDA reaction (e.g., as described by Walker, et al., *Nuc. Acids Res.*, supra) failed to produce any detectable amplification products, i.e., the conventional SDA reaction was inhibited by substitution of dUTP for TTP. Therefore, before UDG decontamination could be used in SDA reactions, the question of whether or not an SDA reaction could be developed that allowed amplification to occur in the presence of dUTP had to be addressed. It was not known whether inhibition of amplification was due to interference with restriction endonuclease nicking by incorporation of uracil into the restriction endonuclease recognition site or to some other factor(s), e.g., inability of the enzymes to incorporate dUTP or lack of displacement of dU-containing strands under the reaction conditions of conventional SDA. During the process of making the invention, it was found that incorporation of dU into the HincII restriction site does not prevent nicking by HincII, i.e., the strand which does not contain $dA_S$ is still nicked effectively. Nicking by BsoBI, in SDA reactions employing this restriction enzyme instead of HincII, is also not prevented by dU in the recognition site. It was not determined specifically which steps of the SDA reaction were inhibited in the presence of dUTP, however, by altering the reaction conditions of the conventional SDA reaction Applicants have developed a new SDA reaction in which incorporation of dU does not significantly interfere with amplification of the target sequence. Further, the $KPO_4$ buffer typically used for SDA is compatible with UDG and Ugi activity. While magnesium can be eliminated from the decontamination reaction, it is required for the SDA reaction and for incorporation of dUTP into DNA by SDA.

By altering the reaction conditions of SDA as described herein, it has been discovered that uracil can be incorporated into the isothermally-amplified DNA without inhibition of the amplification reaction. The uracil-containing nucleic acids can then be specifically recognized and inactivated by treatment with UDG. Therefore, if dU is incorporated into isothermally-amplified DNA, any subsequent reactions can first be treated with UDG, rendering any dU containing DNA from previous amplification reactions unamplifiable. The target DNA to be amplified will not contain the dU and will not be affected by the UDG treatment. In addition, Applicants have unexpectedly found that, prior to amplification of the target, UDG can be sufficiently inhibited by treatment with Ugi alone, i.e., without the heat treatment taught in the prior art. Ugi is therefore useful in isothermal amplification reactions as a means for preventing UDG attack on new amplification products. Ugi may simply be added along with amplification enzymes to begin amplification after decontamination with UDG. These two discoveries have allowed the development of the present UDG/Ugi decontamination method for isothermal nucleic acid amplification reactions.

SUMMARY OF THE INVENTION

The present invention provides methods for inactivating contaminating amplicons in isothermal nucleic acid amplification reactions such as SDA. dU is incorporated into the amplicons produced by amplification in the place of thymine (T) using novel SDA reaction conditions. If these amplicons contaminate a subsequent amplification reaction, they may be inactivated as templates (i.e., rendered unamplifiable) by treatment with UDG. As isothermal amplification does not involve elevated temperatures, the UDG may be inactivated during the subsequent amplification of specific target sequences by inclusion of the UDG inhibitor protein Ugi.

The incorporation of the dU residues has unexpectedly been found to enhance the amplification power of SDA as compared to conventional SDA reactions. This enhancement is observed when dU-containing nucleic acids are amplified by SDA (without decontamination by addition of UDG). While not wishing to be bound by any particular theory of how the invention works, it is possible that this enhancement is the result of lower melting temperatures when DNA contains dU. These lower DNA melting temperatures may provide greater primer hybridization specificity and may also enhance strand displacement by the polymerase.

DETAILED DESCRIPTION OF THE INVENTION

Figure 1:
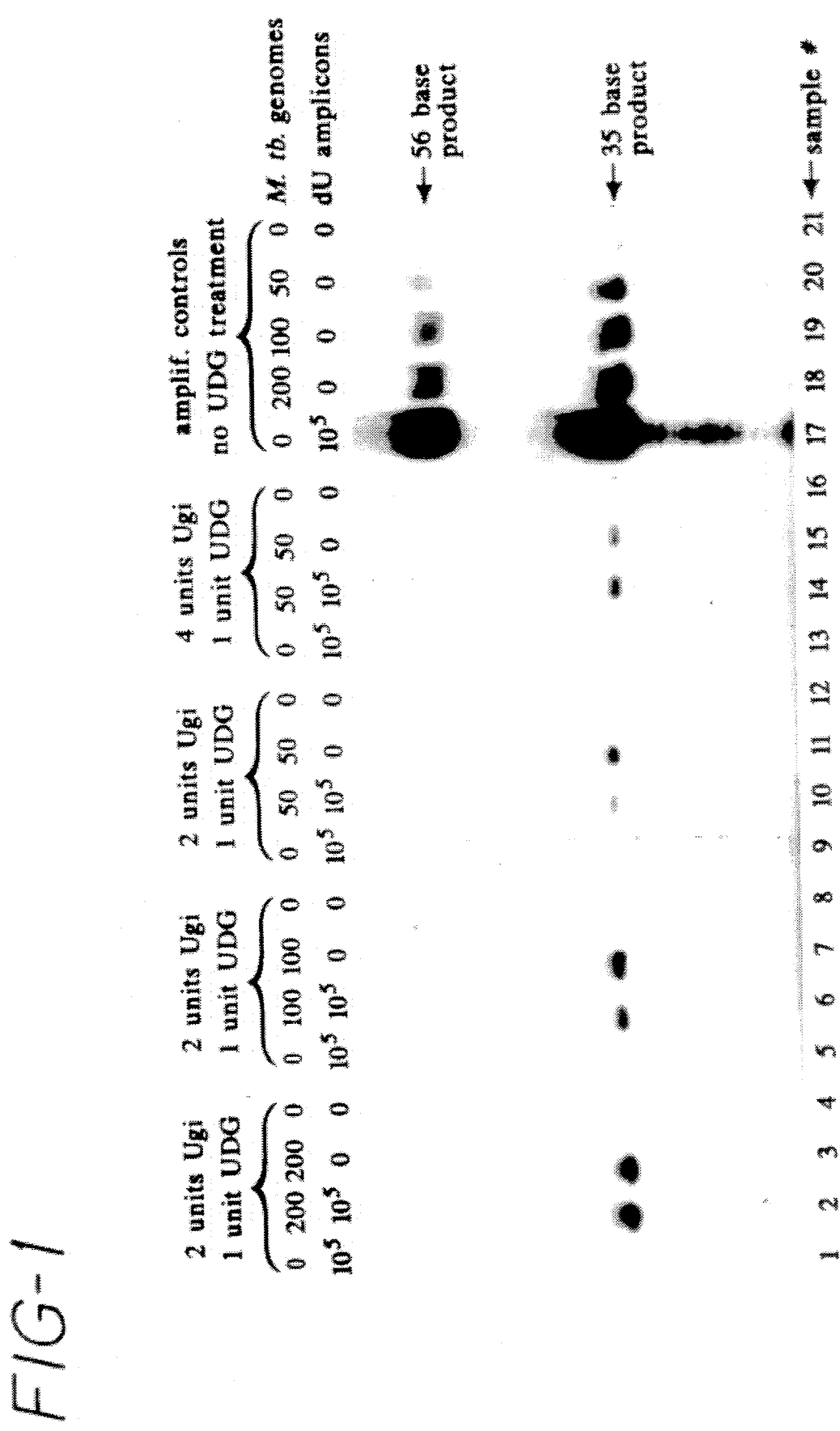
FIG. 1 is an autoradiograph showing the results of Example 1.

The present invention provides methods for preventing amplicons generated from a prior nucleic acid amplification reaction from serving as templates in a subsequent isothermal amplification reaction. The methods include introduction of an unconventional nucleotide into the amplified target sequence and treatment of subsequent samples to specifically remove the unconventional nucleotide prior to amplification of nucleic acids in the sample. Removal of the unconventional nucleotide from the previously generated nucleic acids containing it renders the previously-generated nucleic acid unsuitable for further amplification in the subsequent amplification reaction.

"Unconventional" nucleotides are nucleotides which are not naturally occurring in a particular nucleic acid. Unconventional nucleotides may be naturally occurring nucleotides (e.g., hypoxanthine) or they may be chemically modified derivatives or analogs of conventional nucleotides (e.g., N-7-methylguanine, deoxyuridine and deoxy-3'-methyladenosine). For example, uracil is a naturally occurring and conventional nucleotide in RNA but it is unconventional in DNA. The selected unconventional nucleotide should not inhibit the amplification reaction or subsequent manipulations of the amplified target sequence, i.e., it should not interfere with polymerase, hybridization, etc. Uracil is the preferred unconventional nucleotide for incorporation into DNA according to the methods of the present invention. Uracil is preferably incorporated as 2'-deoxyuridine 5'-triphosphate (dUTP) and may be included in the DNA synthesis reaction during which a target sequence is amplified and/or during synthesis of the primers. Preferably, dUTP is used during amplification (DNA synthesis) at about 0.1–1.0 mM to fully or partially replace TTP. Most preferably, dUTP fully replaces TTP in the amplification reaction and is included at a higher concentration than each of the other three nucleotides to drive the reaction for maximum substitution (e.g., 0.5 mM dUTP and 0.2 mM of each of $dA_STP$, dCTP and dGTP). Longer targets will be more fully dU-substituted than shorter targets for any given concentration of dUTP, and the concentration of dUTP may be adjusted accordingly depending on target length. Magnesium is optional during UDG treatment, but is required for incorporation of dUTP into amplicons during SDA. Magnesium is provided as a magnesium salt, preferably $MgCl_2$ or magnesium acetate ($MgOAc_2$).

There was no detectable amplification when dUTP was simply substituted for TTP in the conventional SDA reaction. Attempts to overcome this problem revealed that several interrelated factors are critical for SDA when dUTP is substituted for TTP. First, it was discovered that a higher concentration of free magnesium than was previously present in SDA reactions was necessary to obtain amplification in the presence of dUTP. Free magnesium concentration is calculated by subtracting the total concentration of dNTPs (including dUTP) from the magnesium concentration. In conventional SDA, free magnesium is about 2 mM (Walker, et al., *Nuc. Acids Res.* and *PNAS*, supra: [6 mM $MgCl_2$ or $MgOAc_2$]—[4 mM dNTPs]=2 mM free $Mg^{2+}$). To incorporate dUTP into SDA-generated amplicons, the free magnesium concentration should be greater than 2 mM, preferably greater than about 4 mM. This free magnesium concentration may be obtained by increasing the concentration of the magnesium salt, decreasing the concentration of dNTPs, or both. For example, the proportions of magnesium salt and dNTPs in the SDA reaction to give a free magnesium concentration greater than about 4 mM may be a) 0.2 mM each dNTP, 0.5 mM dUTP and 6 mM $MgCl_2$ or $MgOAc_2$, b) 0.2 mM each dNTP, 1 mM dUTP and 6 mM $MgCl_2$ or $MgOAc_2$, or c) 0.2–0.6 mM each dNTP, 2 mM dUTP and 8 mM $MgCl_2$ or $MgOAc_2$. In general, the concentration of the magnesium salt will be about 6–10 mM, the concentration of each dNTP (other than dUTP) will be about 0.1–1 mM, and the concentration of dUTP will be about 0.5–4 mM. One skilled in the art, without the exercise of inventive skill, can easily adjust the relative concentrations of these components within the given ranges to obtain reaction mixtures other than those exemplified which also have the appropriate free magnesium concentration.

In addition to modifying the relative concentrations of magnesium and dNTPs in the conventional SDA reaction, it was discovered that the type and concentration of cosolvent had a significant effect on SDA in the presence of dUTP. In general, a higher concentration of cosolvent was required as compared to conventional SDA, which employed about 3% 1-methyl 2-pyrrolidinone (NMP; Walker, et al., *Nuc. Acids Res.*, supra). About 3% glycerol was also present in the conventional reaction due to its inclusion in the enzyme solutions. However, SDA did not occur under these conventional conditions when dUTP was substituted for TTP. Applicants have found that increasing the glycerol cosolvent to about 7%–20% (including the glycerol added with the enzymes) or using about 3%–9% dimethylsulfoxide (DMSO) as a cosolvent allows SDA to proceed in the presence of dUTP. It was particularly unexpected that the high concentration of glycerol did not detectably interfere with specific amplification of the target, as high concentrations of glycerol are often associated with the appearance of "star" activity in restriction endonucleases. In general, glycerol results in less nonspecific background amplification than DMSO and may improve decontamination efficiency when UDG is added. However, Applicants have also observed that DMSO is a better solvent for use in multiplex SDA reactions (simultaneous amplification of multiple targets), although the reasons for this are not known. NMP is also a suitable cosolvent, but has a very narrow useful range of concentration (about 3%) and generally requires a higher concentration of magnesium than is customary for conventional SDA (e.g., at least about 8 mM magnesium salt).

Using the guidelines provided above only routine optimization is required to determine the appropriate relative concentrations of dUTP, magnesium and cosolvent for any particular SDA reaction to produce full dU-substitution of the amplification product. The other components of the conventional SDA reaction (e.g., restriction endonuclease, polymerase, buffer, etc.) may be included as in the conventional SDA reaction mixture. The process steps of the amplification reaction are also performed according to conventional SDA protocols.

In general, all amplification reactions in a laboratory will be performed with incorporation of dUTP so that all subsequent amplifications can be decontaminated prior to amplification. For example, amplicons from a prior SDA reaction performed with incorporation of dU can be rendered unamplifiable by UDG in a subsequent SDA reaction also performed with incorporation of dU to generate amplicons which can be rendered unamplifiable if they contaminate a second subsequent SDA reaction. To decontaminate a sample prior to amplification, 0.1–10 units of UDG, preferably 1–2 units of UDG, are added to the sample and to non-enzymatic amplification reagents (including dUTP) for 5–30 min. at 25°–45° C., preferably about 41° C. Following incubation with UDG, the remaining enzymatic components of the amplification are added with about 0.1–50 units of Ugi, preferably 1–4 units of Ugi, to begin the amplification reaction. The ratio of UDG:Ugi should be at least 1:1 or greater, preferably about 1:4. The appropriate amount of Ugi to inactivate the UDG present in the reaction may easily be determined empirically. Addition of Ugi alone is sufficient to inactivate UDG in the reaction and prevent removal of uracil residues from the newly synthesized amplicons. Heat inactivation of UDG is not required, making Ugi particularly useful in isothermal amplification reactions such as SDA.

Amplified target sequences (amplicons) may then be detected using methods known in the art. They may be identified by a characteristic size, for example by gel electrophoresis, or they may be visualized by hybridization to oligonucleotide probes tagged with a detectable label. A preferred method for detecting amplicons is the primer extension method described by Walker, et al. (*Nuc. Acids Res.*, supra), in which a $^{32}$-P labeled primer is specifically hybridized to the amplicon and extended with polymerase. An extended primer of the predicted size is then visualized by autoradiography after gel electrophoresis of the primer extension products.

UDG is found in many cells, and may contaminate reagents used in nucleic acid laboratory protocols (e.g., restriction enzymes, polymerases, ligases, etc.) The present invention also provides a method for assaying samples and reagents for UDG activity. Such an assay is useful for identifying sources of UDG contamination which may attack uracil-containing DNA. To assay for UDG activity in a sample or a reagent according to the invention, known uracil-containing target nucleic acids are added to the sample or reagent to be tested. The sample or reagent is incubated for a sufficient period of time to allow any contaminating UDG to remove uracil from the target nucleic acids and render them unamplifiable. Ugi is added and the target nucleic acids are amplified as described above. The amplification products, if any, are then detected. If UDG is present in the sample or reagent, no amplification products or a reduced amount of amplification products will be detected. If no UDG is present, amplification of the target nucleic acids will proceed normally.

EXAMPLE 1

This experiment examined the effect of UDG treatment on the amplification of samples containing various amounts (50–200 genomes) of *Mycobacterium tuberculosis* DNA and dU-containing amplicons. dU containing amplicons were produced, as follows, by SDA of a sample containing approximately $1\times10^4$ *Mycobacterium tuberculosis* (M.tb.) genomes. The M.tb. target DNA was amplified in an SDA reaction comprising 50 mM KPO$_4$; 10 µg BSA; 0.2 mM each dA$_S$TP, dCTP and dGTP; 10% glycerol (7% plus 3% contributed by enzyme solutions); 6 mM MgCl$_2$; 0.5 mM dUTP; 0.5 µM amplification primers and 0.05 µM bumper primers. The steps of the amplification reaction were generally as described by Walker, et al. *Nuc. Acids Res.*, supra, except that the SDA reaction was run at 41° C. After amplification, it was estimated that the reaction contained approximately $5.1\times10^{11}$ dU-containing amplicons/µl. This preparation was used as the stock source of contaminating amplicons for spiking into new samples, and was diluted as necessary to produce the required number of molecules for each sample.

*Mycobacterium tuberculosis* DNA and/or $10^5$ dU amplicons were contained in 42 µl of reaction buffer as described in Table 1. Reactions were grouped in fours to examine the effect of UDG treatment on the amplicons in the presence or absence of various amounts of genomic M.tb. DNA. If the UDG treatment was unsuccessful or only partially successful in eliminating the amplicons, amplification products would be detected in the first sample of each group (samples 1, 5, 9 and 13). Reaction buffer contained K$_i$PO$_4$, bovine serum albumin, four primers (SEQ ID NO:1, SEQ ID NO:2, SEQ ID NO:3 and SEQ ID NO:4), glycerol, dA$_S$TP, dCTP and dGTP, but dUTP was substituted for TTP as described above. The samples were denatured at 98° C. for 3 minutes, cooled to 42° C. and 2 µl of 0.5 unit/µl UDG was added. In the control samples, 2 µl of 25% glycerol was added. All samples were incubated at 42° C. for 30 minutes and then the temperature was adjusted to 41° C. SDA amplification was begun by adding 6 µl of an enzyme mix containing MgCl$_2$, exonuclease free Klenow, Hinc II, and 2 or 4 units of the UDG inhibitor (Ugi). The amplification reaction was incubated at 41° C. for 2 hours and terminated by heating at 72° C. for 2 minutes. The final concentration of the reaction components after the addition of the enzyme mix was as follows: 50 mM K$_i$PO$_4$ pH 7.5; 0.2 mM each dA$_S$TP, dCTP, dGTP; 0.5 mM dUTP; 0.5 µM SDA amplification primers 1 and 2 (SEQ ID NO:1 and SEQ ID NO:2); 0.05 uM SDA bumper primers 3 and 4 (SEQ ID NO:3 and SEQ ID NO:4); 0.1 ug/ul bovine serum albumin; 7 mM MgCl$_2$, 14% glycerol; 1 unit UDG; 2 or 4 units UDG inhibitor; 1 unit exonuclease free Klenow; 150 units Hinc II; 50 ng Human DNA (diluent for Mtb, amplicon DNA)

The products of the UDG/SDA reaction were detected by extension of a $^{32}$P-labelled probe (SEQ ID NO:5) and gel electrophoresis analysis as previously described (Walker, et al. *Nuc. Acids Res.*, supra). The amplification products were detected as two bands on the autoradiograph corresponding to 35 bases and 56 bases.

TABLE 1

| # | +/− amplicons | Mtb genomes | 1U UDG | Ugi |
|---|---|---|---|---|
| 1 | +10$^5$ | 0 | yes | 2 U |
| 2 | +10$^5$ | 200 genomes | yes | 2 U |
| 3 | 0 | 200 genomes | yes | 2 U |
| 4 | 0 | 0 | yes | 2 U |
| 5 | +105 | 0 | yes | 2 U |
| 6 | +10$^5$ | 100 genomes | yes | 2 U |
| 7 | 0 | 100 genomes | yes | 2 U |
| 8 | 0 | 0 | yes | 2 U |
| 9 | +10$^5$ | 0 | yes | 2 U |
| 10 | +10$^5$ | 50 genomes | yes | 2 U |
| 11 | 0 | 50 genomes | yes | 2 U |
| 12 | 0 | 0 | yes | 2 U |
| 13 | +10$^5$ | 0 | yes | 4 U |
| 14 | +10$^5$ | 50 genomes | yes | 4 U |
| 15 | 0 | 50 genomes | yes | 4 U |
| 16 | 0 | 0 | yes | 4 U |
| 17 | +10$^5$ | 0 | no | 2 U |
| 18 | 0 | 200 genomes | no | 2 U |
| 19 | 0 | 100 genomes | no | 2 U |
| 20 | 0 | 50 genomes | no | 2 U |
| 21 | 0 | 0 | no | 2 U |

The results of this experiment are shown in FIG. 1. No amplification products were detected in samples 1, 5, 9 and 13, indicating successful decontamination of the samples. Sample 17 was a no-UDG control and the amplification products detected indicated that $10^5$ contaminating amplicons can be detectably amplified by SDA in the absence of UDG decontamination. Comparing sample 17 to samples 1, 5, 9 and 13 provided a measure of the number of amplicons that can be eliminated by the UDG treatment. The second sample in each group of four (samples 2, 6, 10 and 14) provided a measure of the effect of UDG treatment on the amplification of genomic DNA, i.e., genomic DNA was successfully amplified with only a slight loss in signal (compare samples 2, 6, 10 and 14 with the appropriate control of genomic DNA amplified without UDG treatment—samples 18, 19 and 20). The third sample in each group was a control which measured the effect of UDG treatment in the absence of amplicons on the amplification of genomic DNA. That is, if all of the amplicons in samples 2, 6, 10 and 14 were eliminated by the UDG treatment, the amount of SDA amplification product for samples 2 and 3; 6 and 7; 10 and 11; and 14 and 15 (the second and third samples in each set) should be equivalent. The amounts of amplification products produced in these sample pairs were equivalent, demonstrating successful elimination of the contaminating amplicons. The fourth sample in each set was also a control which monitored background (inadvertent) amplicon contamination that might be added to the SDA reaction with the SDA reagents. These samples contained only 50 ng of human DNA (used as a diluent) which is not specifically amplified by the SDA primers. Samples 4, 8, 12 and 16 were completely free of amplification products. However, sample 21, which received no UDG treatment, showed a weak amplification product signal. The presence of amplification product in sample 21 indicated that the buffer mix had been accidentally contaminated by a low level of amplicons (less than the equivalent of 50 genomes). Comparing this lane to the fourth lane in the UDG treated sets (samples 4, 8, 12 and 16) demonstrated that the background amplicons were also eliminated from the samples by UDG. These experiments demonstrated that as many as $10^5$ dU-containing contaminant amplicons can be eliminated, while still allowing successful amplification of as few as 50 M.tb genomes.

EXAMPLE 2

This experiment examined the effect of $MgCl_2$ on the UDG treatment of $10^5$ contaminating amplicons and the effect of time on the treatment. The dU containing amplicons were those generated by SDA amplification in Example 1. After amplification it was estimated that the reaction contained $5.1\times10^{11}$ amplicons/μl. The amplicons were diluted as needed to provide the $1\times10^5$ dU amplicons used to evaluate UDG decontamination.

Reaction mixes (42 μl) contained $K_iPO_4$ pH 7.5, bovine serum albumin, dUTP, $dA_STP$, dCTP, dGTP, primers 1–4 (SEQ ID NO:1, SEQ ID NO:2, SEQ ID NO:3 and SEQ ID NO:4), and glycerol. In addition, this mix contained ±$MgCl_2$, ±dU and M.tb. genomic DNA as indicated in Table 2. The samples were heated at 98° C. for 3 minutes to denature the DNA and then cooled to 42° C. Two microliters of 0.5 units/μl UDG was added as indicated in Table 2 and allowed to incubate for 5 minutes, 15 minutes or 30 minutes. Enzyme mixtures were prepared containing +/– $MgCl_2$, Hinc II, exonuclease free Klenow and Ugi. Six microliters of enzyme mixture was added to the samples after UDG treatment to begin the SDA amplification reaction. Samples were incubated at 41° C. for 2 hours and amplification was terminated by heating for 2 minutes at 72° C. The final concentration of all the reaction components after the addition of the enzyme mix was as follows: 50 mM $K_iPO_4$ pH 7.5; 0.2 mM each $dA_STP$, dCTP, dGTP; 0.5 mM dUTP; 0.5 μM SDA amplification primers 1 and 2 (SEQ. I.D. NO:1 and SEQ ID NO:2); 0.05 μM primers 3 and 4 (SEQ ID NO:3 and SEQ ID NO:4); 0.1 μg/μl bovine serum albumin; 7 mM $MgCl_2$; 14% glycerol; 1 unit UDG; 2 units Ugi; 1 unit exonuclease free Klenow; 150 units Hinc II; 50 ng human DNA (diluent for amplicons and M.tb. DNA).

The products of the UDG/SDA reaction were detected by extension of a $^{32}$P-labelled probe (SEQ ID NO:5) and gel electrophoresis analysis as in Example 1. The SDA amplification products were detected as two bands on an autoradiograph, corresponding to 35 bases and 56 bases.

TABLE 2

| # | +/– amplicons | +/– 50 genomes | UDG time | +/– $MgCl_2$ during treatment UDG |
|---|---|---|---|---|
| 1 | +$10^5$ | 0 | 5 min | +$MgCl_2$ |
| 2 | +$10^5$ | +50 genomes | 5 min | +$MgCl_2$ |
| 3 | 0 | +50 genomes | 5 min | +$MgCl_2$ |
| 4 | +$10^5$ | 0 | 5 min | –$MgCl_2$ |
| 5 | +$10^5$ | +50 genomes | 5 min | –$MgCl_2$ |
| 6 | 0 | +50 genomes | 5 min | –$MgCl_2$ |
| 7 | +$10^5$ | 0 | 15 min | +$MgCl_2$ |

TABLE 2-continued

| # | +/– amplicons | +/– 50 genomes | UDG time | +/– $MgCl_2$ during treatment UDG |
|---|---|---|---|---|
| 8 | +$10^5$ | +50 genomes | 15 min | +$MgCl_2$ |
| 9 | 0 | +50 genomes | 15 min | +$MgCl_2$ |
| 10 | +$10^5$ | 0 | 15 min | –$MgCl_2$ |
| 11 | +$10^5$ | +50 genomes | 15 min | –$MgCl_2$ |
| 12 | 0 | +50 genomes | 15 min | –$MgCl_2$ |
| 13 | +$10^5$ | 0 | 30 min | +$MgCl_2$ |
| 14 | +$10^5$ | +50 genomes | 30 min | +$MgCl_2$ |
| 15 | 0 | +50 genomes | 30 min | +$MgCl_2$ |
| 16 | +$10^5$ | 0 | 30 min | –$MgCl_2$ |
| 17 | +$10^5$ | +50 genomes | 30 min | –$MgCl_2$ |
| 18 | 0 | +50 genomes | 30 min | –$MgCl_2$ |
| 19 | 0 | +50 genomes | no UDG | +$MgCl_2$ |
| 20 | 0 | +50 genomes | no UDG | –$MgCl_2$ |

Figure 2:
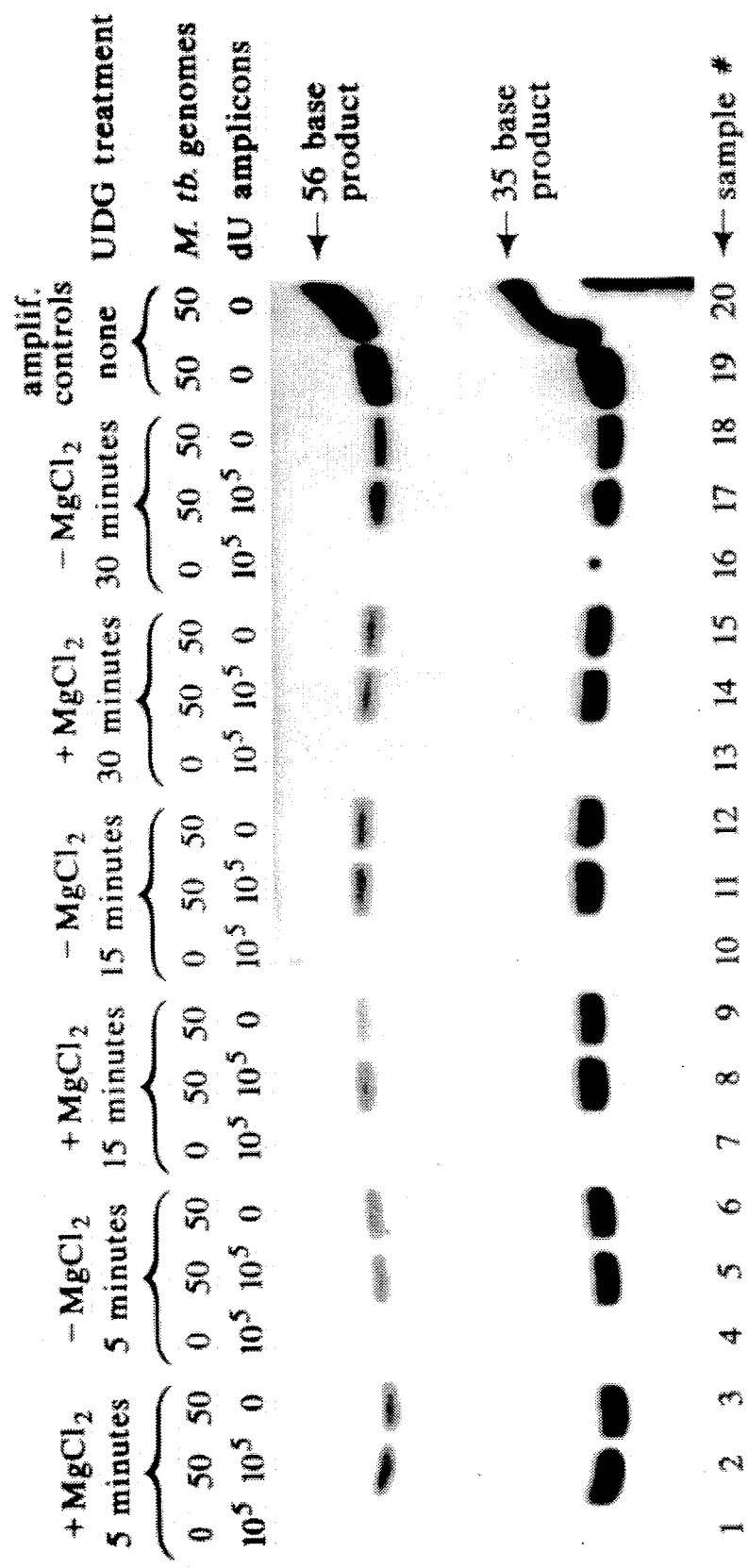
FIG. 2 is an autoradiograph showing the results of Example 2.

The results are shown in FIG. 2. The reactions were grouped in sets of three to examine the effect of $MgCl_2$ and time on the ability of the UDG enzyme to effectively eliminate $10^5$ dU amplicons. If the UDG treatment was unsuccessful or only partially successful the first sample in each set (samples 1, 4, 7, 10, 13 and 16) would contain amplification products. The absence of amplification products in samples 1, 4, 7, 10, 13 and 16 indicated that the UDG enzyme was able to eliminate $10^5$ contaminating dU amplicons under all of the conditions tested. As was also shown in Example 1, the presence of amplification products in the second sample of each set (samples 2, 5, 8, 11, 14 and 17) demonstrated the ability of SDA to amplify genomic DNA in the presence of UDG treated amplicons even in the absence of a heating step between the UDG treatment and the SDA reaction. The prior art relating to the PCR has taught that the heating step was necessary not only to inactivate the UDG enzyme but to cause the abasic, UDG treated DNA to be fragmented into smaller, non-amplifiable segments. Applicants have determined that this heating step is not necessary and have discovered that Ugi alone is sufficient to inactivate UDG. This indicates that the abasic but intact DNA is not amplified under the conditions tested. The third sample in each set (samples 3, 6, 9, 12, 15 and 18) was a control to measure the effect of the UDG treatment on the amplification of genomic DNA in the absence of contaminating dU amplicons. Comparison of the amplification products of the second and third samples in each set demonstrated equivalent signals. There is therefore no difference between the amplification of genomic DNA in the presence or absence of UDG treated amplicons. The last two samples were controls (samples 19 and 20) to measure the amplification of 50 genomes of *Mycobacterium tuberculosis* without UDG treatment. The signal from the untreated sample was slightly darker than that of the UDG-treated sample. This difference suggests that SDA amplification is slightly more efficient in the absence of UDG treatment. This example demonstrated that the presence or absence of $MgCl_2$ during UDG treatment has no significant effect on the elimination of $10^5$ contaminating dU amplicons. In addition, a 5 minute incubation was sufficient to eliminate $10^5$ dU amplicons independent of the presence of $MgCl_2$.

What is claimed is:

1. A method for generating uracil-containing amplicons by Strand Displacement Amplification (SDA), the method comprising the steps of:

a) providing a DNA target sequence in an SDA reaction mixture having a free magnesium concentration greater than about 4 mM and comprising about 6–10 mM of a magnesium salt, about 0.5–4 mM dUTP, about 0.1–1 mM each of three deoxynucleoside triphosphates other than dUTP and a cosolvent selected from the group consisting of about 7–20% glycerol, about 3–9% dimethylsulfoxide and about 3% 1-methyl 2-pyrrolidinone, and;

b) amplifying the target DNA in an SDA reaction such that uracil-containing amplicons are generated.

2. The method according to claim 1 further comprising:

a) treating the uracil-containing amplicons with a sufficient amount of uracil DNA glycosylase (UDG) to render the amplicons unamplifiable in a subsequent SDA reaction, and;

b) inactivating the UDG with uracil-DNA glycosylase inhibitor (Ugi) during the subsequent SDA reaction.

3. The method according to claim 2 wherein the SDA reaction mixture comprises about 0.5 mM dUTP, about 6–8 mM $MgCl_2$ or 6–8 mM magnesium acetate and about 10–15% glycerol.

4. The method according to claim 3 wherein SDA is performed in the presence of about 0.5 mM dUTP, about 0.2 mM dCTP, about 0.2 mM dGTP and about 0.2 mM $dA_STP$.

5. The method according to claim 2 wherein the subsequent SDA reaction comprises at least about 4 mM free magnesium and about 6–10 mM of a magnesium salt, about 0.1–1 mM $dA_STP$, about 0.1–1 mM dCTP, about 0.1–1 mM dGTP, about 0.5–4 mM dUTP and a cosolvent selected from the group consisting of about 7–20% glycerol, about 3–9% DMSO and about 3% NMP.

6. The method according to claim 2 wherein the amplicons are treated with about 0.1–10 units of UDG and the UDG is inactivated with about 0.1–50 units of Ugi.

7. The method according to claim 6 wherein the amplicons are treated with about 1–2 units of UDG and the UDG is inactivated with about 1–4 units of Ugi.

8. The method according to claim 1 wherein uracil-containing amplicons are generated from a target sequence of *Mycobacterium tuberculosis*.

9. A method for generating uracil-containing amplicons by Strand Displacement Amplification (SDA) of DNA comprising:

a) providing a DNA target sequence in an SDA reaction mixture having a free magnesium concentration greater than about 4 mM and comprising about 6–10 mM of a magnesium salt, about 0.1–1 mM dUTP, about 0.1–1 mM each of three deoxynucleoside triphosphates other than dUTP and a cosolvent selected from the group consisting of about 7–20% glycerol, about 3–9% dimethylsulfoxide and about 3% 1-methyl 2-pyrrolidinone, and;

b) amplifying the target DNA in an SDA reaction.

10. The method according to claim 9 wherein the SDA reaction mixture comprises about 0.1–1 mM dUTP, about 6–8 mM $MgCl_2$ or 6–8 mM magnesium acetate and about 10–15% glycerol.

11. The method according to claim 10 wherein SDA is performed in the presence of about 0.5 mM dUTP, about 0.2 mM dCTP, about 0.2 mM dGTP and about 0.2 mM $dA_STP$.

12. A method for detecting uracil DNA glycosylase (UDG) activity in a sample by Strand Displacement Amplification (SDA) comprising:

a) adding uracil-containing target nucleic acid to the sample, the target nucleic acid being generated by SDA in a reaction mixture having a free magnesium concentration greater than about 4 mM and comprising about 6–10 mM of a magnesium salt, about 0.5–4 mM dUTP, about 0.1–1 mM of each of three deoxynucleoside triphosphates other than dUTP and a cosolvent selected from the group consisting of about 7–20% glycerol, about 3–9% dimethylsulfoxide and about 3% 1-methyl 2-pyrrolidinone;

b) incubating the target nucleic acid with the sample for a period of time sufficient to allow UDG, if present, to render the target nucleic acid unamplifiable;

c) amplifying the target nucleic acid, and;

d) detecting the absence of amplification or reduced amplification as an indication of UDG activity.

13. A method for generating uracil-containing amplicons by Strand Displacement Amplification (SDA), the method comprising the steps of:

a) providing a target sequence in an SDA reaction mixture comprising a magnesium salt, dUTP, three deoxynucleoside triphosphates other than dUTP and a cosolvent selected from the group consisting of about 7–20% glycerol, about 3–9% dimethylsulfoxide and about 3% 1-methyl 2-pyrrolidinone, the SDA reaction mixture having a free magnesium concentration greater than about 4 mM, and;

b) amplifying the target sequence by SDA such that uracil-containing amplicons are generated.

* * * * *